(12) United States Patent
Jaeschke et al.

(10) Patent No.: US 8,969,338 B2
(45) Date of Patent: Mar. 3, 2015

(54) ETHYNYL DERIVATIVES

(71) Applicant: Hoffmann-La Roche Inc., Nutley, NJ (US)

(72) Inventors: Georg Jaeschke, Basel (CH); Lothar Lindemann, Basel (CH); Antonio Ricci, Birsfelden (CH); Daniel Rueher, Raedersdorf (FR); Heinz Stadler, Basel (CH); Eric Vieira, Frenkendorf (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 245 days.

(21) Appl. No.: 13/628,136

(22) Filed: Sep. 27, 2012

(65) Prior Publication Data

US 2013/0090332 A1    Apr. 11, 2013

(30) Foreign Application Priority Data

Oct. 7, 2011   (EP) ..................................... 11184331

(51) Int. Cl.
| | |
|---|---|
| C07D 401/04 | (2006.01) |
| C07D 401/14 | (2006.01) |
| C07D 403/04 | (2006.01) |
| C07D 413/04 | (2006.01) |
| A61K 31/506 | (2006.01) |
| A61K 31/444 | (2006.01) |
| A61K 31/4439 | (2006.01) |

(52) U.S. Cl.
CPC ............ C07D 401/04 (2013.01); C07D 403/04 (2013.01); C07D 413/04 (2013.01)
USPC ........ 514/228.8; 514/256; 514/333; 514/341; 514/343; 544/96; 544/322; 546/256; 546/274.1; 546/276.1; 546/278.4

(58) Field of Classification Search
CPC .............. A61K 31/506; A61K 31/444; A61K 31/4439; C07D 401/04; C07D 401/14; C07D 403/04; C07D 413/04
USPC ......... 514/228.8, 256, 333, 341, 343; 544/96, 544/322; 546/256, 274.1, 276.1, 278.4
See application file for complete search history.

(56) References Cited

U.S. PATENT DOCUMENTS

| | | | | |
|---|---|---|---|---|
| 8,513,273 | B2 * | 8/2013 | Green et al. | .................... 514/278 |
| 8,618,296 | B2 * | 12/2013 | Green et al. | ..................... 546/15 |
| 2014/0155602 | A1 * | 6/2014 | Green et al. | ................... 544/238 |

FOREIGN PATENT DOCUMENTS

| | | |
|---|---|---|
| JP | H07181440 | 7/1995 |
| JP | H09151179 | 6/1997 |
| WO | 0218353 | 3/2002 |
| WO | 2005/044797 | 5/2005 |
| WO | 2006/048771 | 5/2006 |
| WO | 2006/129199 | 12/2006 |
| WO | 2008/151184 | 12/2008 |
| WO | 2011/051201 | 5/2011 |

OTHER PUBLICATIONS

The English translation of the Taiwanese Office Action, issued on Dec. 25, 2013, in the corresponding Taiwanese application No. 101136749.
Boer et al., Neuroscience(156):203-215 ( 2008).
Bach et al., Expert Opinion Therapeutic Patents (XP002552836), 17(4):371-384 ( 2007).
(International Search Report for PCT/EP2012/069599 Nov. 15, 2012).
Rocher et al., Curr. Topics in Medicinal Chemistry 11(6):680-695 ( 2011).
Wu et al., Molecular Pharmacology 40:333-336 ( 1991).
Kinney et al., Journal of Pharma & Experimental Ther. 313(1):199-206 ( 2005).
Owen et al., Annual Review of Medicine 62:25-40 ( 2011).

* cited by examiner

Primary Examiner — James O Wilson
Assistant Examiner — Ebenezer O Sackey

(57) ABSTRACT

The present invention relates to ethynyl derivatives of formula I

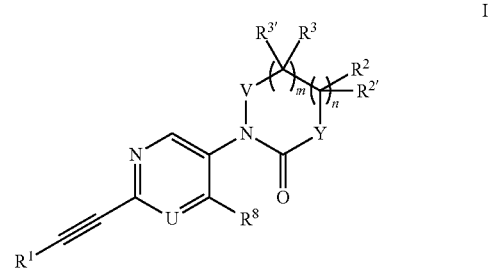

wherein U, V, Y, $R^1$, $R^2$, $R^{2'}$, $R^3$, $R^{3'}$ and $R^8$ are described herein.

It has been found that the compounds of general formula I are allosteric modulators of the metabotropic glutamate receptor subtype 5 (mGluR5).

12 Claims, No Drawings

ETHYNYL DERIVATIVES

PRIORITY TO RELATED APPLICATION(S)

This application claims the benefit of European Patent Application No. 11184331.4, filed Oct. 7, 2011, which is hereby incorporated by reference in its entirety.

FIELD OF THE INVENTION

The present invention relates to compounds of formula I and to their pharmaceutically acceptable salts, in cases where this applies to mixtures of enantiomers or diastereomers or their enantiomerically or diastereomerically pure forms, to these compounds as pharmaceutically active substances, to the processes for their production as well as to the use in the treatment or prevention of disorders, relating to allosteric modulators for the mGluR5 receptor, such as schizophrenia, cognition, fragile X syndrome or autism, and to pharmaceutical compositions containing the compounds of formula I.

BACKGROUND OF THE INVENTION

In the central nervous system (CNS) the transmission of stimuli takes place by the interaction of a neurotransmitter, which is sent out by a neuron, with a neuroreceptor.

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of O-protein coupled receptors.

At present, eight different members of these mGluR are known and of these some even have sub-types. According to their sequence homology, signal transduction mechanisms and agonist selectivity, these eight receptors can be sub-divided into three sub-groups:
mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, epilepsy, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are ischemia, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depressions.

Disorders mediated full or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression, pain and drug dependency (*Expert Opin. Ther. Patents* (2002), 12, (12)).

A new avenue for developing selective modulators is to identify compounds which act through allosteric mechanism, modulating the receptor by binding to a site different from the highly conserved orthosteric binding site. Allosteric modulators of mGluR5 have emerged recently as novel pharmaceutical entities offering this attractive alternative. Allosteric modulators have been described, for example in WO2008/151184, WO2006/048771, WO2006/129199 and WO2005/044797 and in *Molecular Pharmacology*, 40, 333-336, 1991; *The Journal of Pharmacology and Experimental Therapeutics*, Vol 313, No. 1, 199-206, 2005; In recent years there have been significant advantages in understanding the pathophysiology of several disorders of brain development, suggesting that protein synthesis at synapses is triggered by activation of group I metabotropic glutamate receptors. Such disorders include fragile X syndrome, autism, idiopatic autism, tuberous sclerosis complex disorder, neurofibromatosis type I or Rett syndrome (*Annu. Rev. Med.*, 2011, 62, 31.1-31.19 and *Neuroscience* 156, 2008, 203-215).

Described in the prior art are positive allosteric modulators. They are compounds that do not directly activate receptors by themselves, but markedly potentiate agonist-stimulated responses, increase potency and maximum of efficacy. The binding of these compounds increases the affinity of a glutamate-site agonist at its extracellular N-terminal binding site. Allosteric modulation is thus an attractive mechanism for enhancing appropriate physiological receptor activation. There is a scarcity of selective allosteric modulators for the mGluR5 receptor. Conventional mGluR5 receptor modulators typically lack satisfactory aqueous solubility and exhibit poor oral bioavailability.

Therefore, there remains a need for compounds that overcome these deficiencies and that effectively provide selective allosteric modulators for the mGluR5 receptor.

SUMMARY OF THE INVENTION

There are provided compounds of the formula

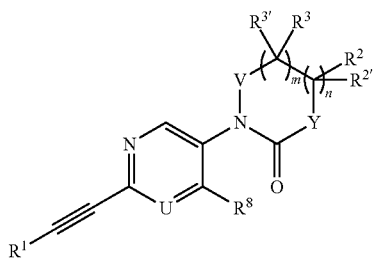

wherein U, V, Y, $R^1$, $R^2$, $R^{2'}$, $R^3$, $R^{3'}$ and $R^8$ are described herein.

DETAILED DESCRIPTION OF THE INVENTION

The present invention relates to ethynyl derivatives of formula I

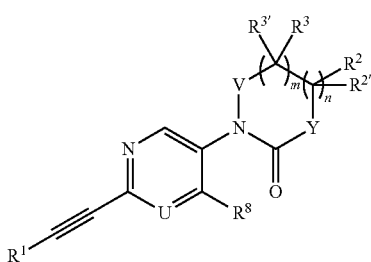

wherein
U is N or CH,
R⁸ is hydrogen, halogen, lower alkyl or lower alkoxy;
Y is —N(R⁴)—, —O— or —C(R⁵R⁵')—;
   wherein R⁴ is hydrogen or lower alkyl and R⁵/R⁵' are independently hydrogen, hydroxy, lower alkyl or lower alkoxy;
V is —N(R⁶)— or —C(R⁷R⁷'), wherein R⁶ is hydrogen or lower alkyl and R⁷/R⁷' are independently from each other hydrogen, lower alkyl, CH₂-lower alkoxy or may form together with the carbon atom to which they are attached a C₃-C₆-cycloalkyl;
R¹ is phenyl or heteroaryl, which are optionally substituted by halogen, lower alkyl or lower alkoxy;
m is 0 or 1 and in case m is 1,
R³/R³' are independently from each other hydrogen, lower alkyl, CH₂-lower alkoxy or may form together with the carbon atom to which they are attached a C₃-C₆-cycloalkyl;
n is 0 or 1 and in case n is 1,
R²/R²' are independently hydrogen, lower alkyl or CH₂-lower alkoxy or may form together with the carbon atom to which they are attached a C₃-C₆-cycloalkyl;
or if m is 1 and n is 0, R³ and R⁷ may form together with the carbon atoms to which they are attached a C₄₋₆-cycloalkyl;
or if m is 1 and n is 1, R² and R³ or R³ and R⁷ may form together with the carbon atoms to which they are attached a C₄₋₆-cycloalkyl;
or a pharmaceutically acceptable acid addition salt, a racemic mixture, or its corresponding enantiomer and/or optical isomer and/or stereoisomer thereof.

It has now surprisingly been found that the compounds of general formula I are allosteric modulators of the metabotropic glutamate receptor subtype 5 (mGluR5).

Compounds of formula I are distinguished by having valuable therapeutic properties. They can be used in the treatment or prevention of disorders, relating to allosteric modulators for the mGluR5 receptor.

The most preferred indications for compounds which are allosteric modulators are schizophrenia and cognition.

DEFINITIONS

The following definitions of the general terms used in the present description apply irrespective of whether the terms in question appear alone or in combination.

As used herein, the term "lower alkyl" denotes a saturated, i.e. aliphatic hydrocarbon group including a straight or branched carbon chain with 1-4 carbon atoms. Examples for "alkyl" are methyl, ethyl, n-propyl, and isopropyl.

The term "alkoxy" denotes a group —O—R' wherein R' is lower alkyl as defined above.

The term "ethynyl" denotes the group —C|C—.

The term "cycloalkyl" denotes a saturated carbon ring, containing from 3 to 6 carbon ring atoms, for example cyclopropyl, cyclobutyl, cyclopentyl or cyclohexyl.

The term "heteroaryl" denotes a 5 or 6-membered aromatic ring, containing at least one N, O or S-heteroatom, for example pyridinyl, pyrimidinyl, pyrazolyl, pyridazinyl, imidazolyl, triazolyl, thienyl or pyrazinyl.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

One embodiment of the invention are compounds of formula

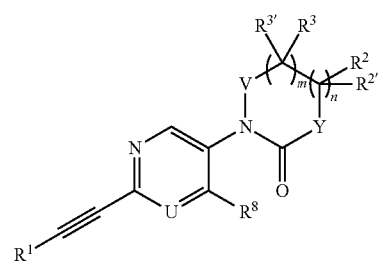

wherein
U is N or CH;
R⁸ is hydrogen;
Y is CH₂, O, —N(CH₃)— or —N(CH₂CH₃)—;
V is CH₂, —NH— or —N(CH₃)—;
R¹ is phenyl or pyridinyl, which are optionally substituted by halogen;
m is 0 or 1 and in case m is 1,
R³/R³' are independently from each other hydrogen or lower alkyl,
n is 1;
R²/R²' are independently from each other hydrogen or lower alkyl;
or a pharmaceutically acceptable acid addition salt, a racemic mixture, or its corresponding enantiomer and/or optical isomer and/or stereoisomer thereof,
for example the following compounds
4,4-Dimethyl-1-(6-phenylethynyl-pyridin-3-yl)-pyrrolidin-2-one
6,6-Dimethyl-3-(6-phenylethynyl-pyridin-3-yl)-[1,3]oxazinan-2-one
3,4,4-Trimethyl-1-(6-phenylethynyl-pyridin-3-yl)-imidazolidin-2-one
1-[6-(4-Fluoro-phenylethynyl)-pyridin-3-yl]-3,4,4-trimethyl-imidazolidin-2-one
1-[6-(3-Fluoro-phenylethynyl)-pyridin-3-yl]-3,4,4-trimethyl-imidazolidin-2-one
3,4,4-Trimethyl-1-(6-pyridin-3-ylethynyl-pyridin-3-yl)-imidazolidin-2-one
1-[6-(3-Fluoro-phenylethynyl)-pyridin-3-yl]-4,4-dimethyl-pyrrolidin-2-one
5,5-Dimethyl-2-(6-phenylethynyl-pyridin-3-yl)-pyrazolidin-3-one
4,4-Dimethyl-1-(6-phenylethynyl-pyrimidin-3-yl)-pyrrolidin-2-one
3,4,4-Trimethyl-1-(2-phenylethynyl-pyrimidin-5-yl)-imidazolidin-2-one 3-Ethyl-4,4-dimethyl-1-(2-phenylethynyl-pyrimidin-5-yl)-imidazolidin-2-one 1,5,5-Trimethyl-2-(6-phenylethynyl-pyridin-3-yl)-pyrazolidin-3-one 2-[6-(3-Fluoro-phenylethynyl)-pyridin-3-yl]-1,5,5-trimethyl-pyrazolidin-3-one 2-[6-(2,5-Difluoro-phenylethynyl)-pyridin-3-yl]-1,5,5-trimethyl-pyrazolidin-3-one 2-[6-(3-Fluoro-phenylethynyl)-pyridin-3-yl]-5,5-dimethyl-pyrazolidin-3-one or 2-[6-(2,5-Difluoro-phenylethynyl)-pyridin-3-yl]-5,5-dimethyl-pyrazolidin-3-one.

One further embodiment of the invention are compounds of formula

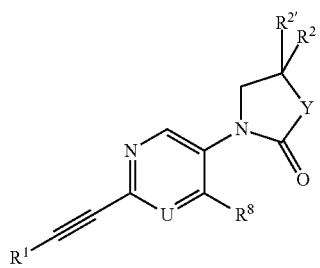

IA wherein
U is N or CH,
$R^8$ is hydrogen, halogen, lower alkyl or lower alkoxy;
Y is —N($R^4$)—, O or —C($R^5R^5$)—';
  wherein $R^4$ is hydrogen or lower alkyl and $R^5/R^{5'}$ are independently hydrogen, hydroxy, lower alkyl or lower alkoxy;
$R^1$ is phenyl or heteroaryl, which are optionally substituted by halogen, lower alkyl or lower alkoxy;
$R^2/R^{2'}$ are independently from each other hydrogen, lower alkyl, $CH_2$-lower alkoxy or may form together with the carbon atom to which they are attached a $C_3$-$C_6$-cycloalkyl;
or a pharmaceutically acceptable acid addition salt, a racemic mixture, or its corresponding enantiomer and/or optical isomer and/or stereoisomer thereof.

Examples of compounds of formula IA are the followings:

4,4-dimethyl-1-(6-phenylethynyl-pyridin-3-yl)-pyrrolidin-2-one 3,4,4-trimethyl-1-(6-phenylethynyl-pyridin-3-yl)-imidazolidin-2-one 1-[6-(4-fluoro-phenylethynyl)-pyridin-3-yl]-3,4,4-trimethyl-imidazolidin-2-one 1-[6-(3-fluoro-phenylethynyl)-pyridin-3-yl]-3,4,4-trimethyl-imidazolidin-2-one 3,4,4-trimethyl-1-(6-pyridin-3-ylethynyl-pyridin-3-yl)-imidazolidin-2-one 1-[6-(3-fluoro-phenylethynyl)-pyridin-3-yl]-4,4-dimethyl-pyrrolidin-2-one 4,4-dimethyl-1-(6-phenylethynyl-pyrimidin-3-yl)-pyrrolidin-2-one 3,4,4-Trimethyl-1-(2-phenylethynyl-pyrimidin-5-yl)-imidazolidin-2-one or 3-Ethyl-4,4-dimethyl-1-(2-phenylethynyl-pyrimidin-5-yl)-imidazolidin-2-one.

A further embodiment of the invention are compounds of formula

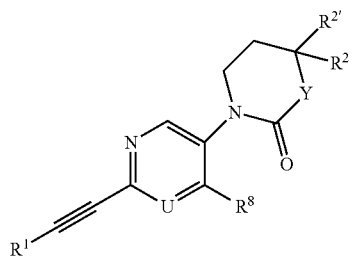

IB wherein
U is N or CH,
$R^8$ is hydrogen, halogen, lower alkyl or lower alkoxy;
Y is —N($R^4$)—, O or —C($R^5R^{5'}$)—;
  wherein $R^4$ is hydrogen or lower alkyl and $R^5/R^{5'}$ are independently hydrogen, hydroxy, lower alkyl or lower alkoxy;
$R^1$ is phenyl or heteroaryl, which are optionally substituted by halogen, lower alkyl or lower alkoxy;
$R^2R^{2'}$ are independently from each other hydrogen, lower alkyl, $CH_2$-lower alkoxy or may form together with the carbon atom to which they are attached a $C_3$-$C_6$-cycloalkyl;
or a pharmaceutically acceptable acid addition salt, a racemic mixture, or its corresponding enantiomer and/or optical isomer and/or stereoisomer thereof.

Specific examples from compounds of formula IB is the following:

6,6-dimethyl-3-(6-phenylethynyl-pyridin-3-yl)-[1,3]oxazinan-2-one.

A further embodiment of the invention are compounds of formula

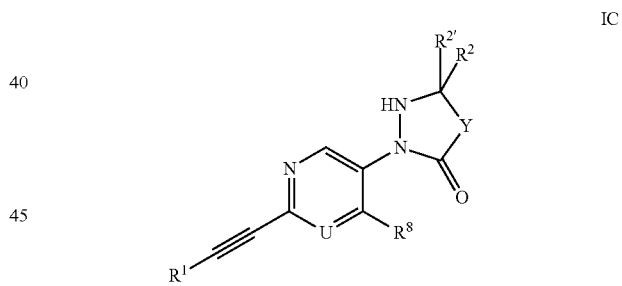

IC wherein
U is N or CH,
$R^8$ is hydrogen, halogen, lower alkyl or lower alkoxy;
Y is —N($R^4$)—, O or —C($R^5R^{5'}$)—;
  wherein $R^4$ is hydrogen or lower alkyl and $R^5/R^{5'}$ are independently hydrogen, hydroxy, lower alkyl or lower alkoxy;
$R^1$ is phenyl or heteroaryl, which are optionally substituted by halogen, lower alkyl or lower alkoxy;
$R^2/R^{2'}$ are independently from each other hydrogen, lower alkyl, $CH_2$-lower alkoxy or may form together with the carbon atom to which they are attached a $C_3$-$C_6$-cycloalkyl;
or a pharmaceutically acceptable acid addition salt, a racemic mixture, or its corresponding enantiomer and/or optical isomer and/or stereoisomer thereof.

Examples from compounds of formula IC is the following:

5,5-dimethyl-2-(6-phenylethynyl-pyridin-3-yl)-pyrazolidin-3-one.

One further embodiment of the invention are compounds of formula

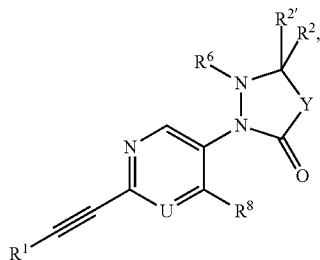

wherein
U is N or CH,
R$^8$ is hydrogen, halogen, lower alkyl or lower alkoxy;
Y is —N(R$^4$)—, —O— or —C(R$^5$R$^{5'}$)—;
  wherein R$^4$ is hydrogen or lower alkyl and R$^5$/R$^{5'}$ are independently hydrogen, hydroxy, lower alkyl or lower alkoxy;
R$^6$ is hydrogen or lower alkyl
R$^1$ is phenyl or heteroaryl, which are optionally substituted by halogen, lower alkyl or lower alkoxy:
R$^2$/R$^{2'}$ are independently from each other hydrogen, lower alkyl, CH$_2$-lower alkoxy or may form together with the carbon atom to which they are attached a C$_3$-C$_6$-cycloalkyl;
or a pharmaceutically acceptable acid addition salt, a racemic mixture, or its corresponding enantiomer and/or optical isomer and/or stereoisomer thereof.

Examples of compounds of formula I-D are
1,5,5-Trimethyl-2-(6-phenylethynyl-pyridin-3-yl)-pyrazolidin-3-one
2-[6-(3-Fluoro-phenylethynyl)-pyridin-3-yl]-1,5,5-trimethyl-pyrazolidin-3-one
2-[6-(2,5-Difluoro-phenylethynyl)-pyridin-3-yl]-1,5,5-trimethyl-pyrazolidin-3-one
2-[6-(3-Fluoro-phenylethynyl)-pyridin-3-yl]-5,5-dimethyl-pyrazolidin-3-one or
2-[6-(2,5-Difluoro-phenylethynyl)-pyridin-3-yl]-5,5-dimethyl-pyrazolidin-3-one.

The preparation of compounds of formula I of the present invention may be carried out in sequential or convergent synthetic routes. Syntheses of the compounds of the invention are shown in the following schemes 1 and 2. The skills required for carrying out the reaction and purification of the resulting products are known to those skilled in the art. The substituents and indices used in the following description of the processes have the significance given herein before.

The compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts may be prepared by methods, known in the art, for example by the process variant described below, which process comprises a) reacting a compound of formula

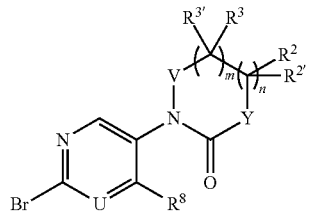

with a suitable aryl-acetylene of formula

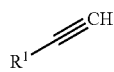

to a compound of formula

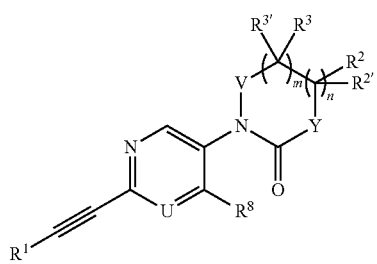

wherein the substituents are described above, or b) reacting a compound of formula

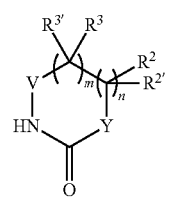

with a suitable compound of formula

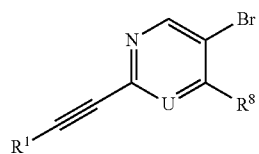

to a compound of formula

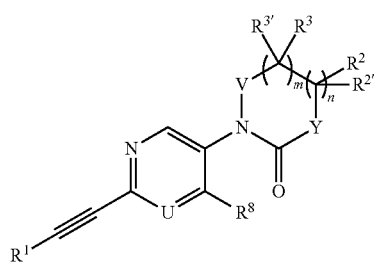

wherein the substituents are described above, and, if desired, converting the compounds obtained into pharmaceutically acceptable acid addition salts.

The preparation of compounds of formula I is further described in more detail in schemes 1 and 2 and in examples 1-16.

Scheme 1

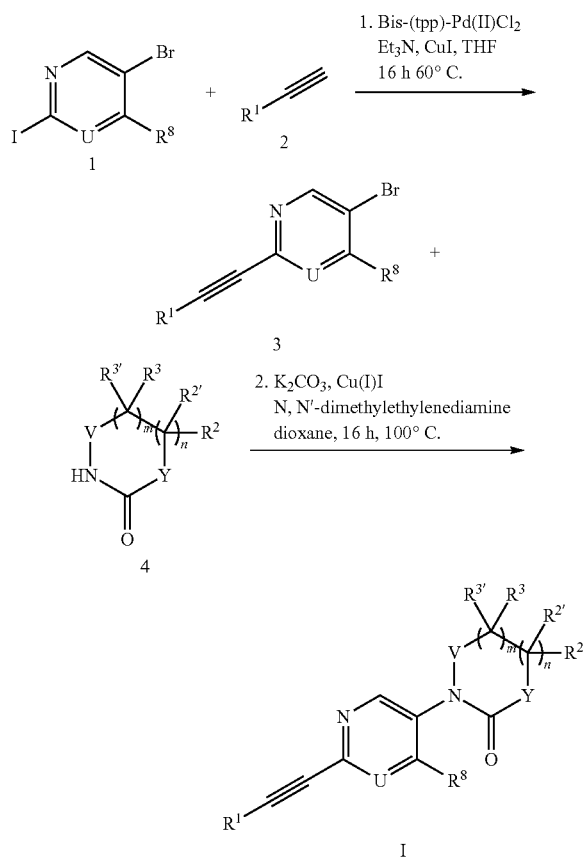

An ethynyl-pyridine or ethynyl-pyrimidine compound of formula I can be obtained for example by Sonogashira coupling of an appropriate 5-bromo-2-iodo-pyridine or pyrimidine 1 with an appropriately substituted arylacetylene 2 to yield the corresponding 5-bromo-2-ethynylpyridine or pyrimidine derivatives 3. Substitution of 3 with an appropriate lactam, cyclic carbamate, cyclic urea or pyrazolidin-3-one derivative 4 in presence of a base such as potassium carbonate and using copper(I)iodide and N,N'-dimethylethylenediamine in a solvent like dioxane yields the desired ethynyl-pyridine or ethynyl-pyrimidine compound of formula I.

Scheme 2

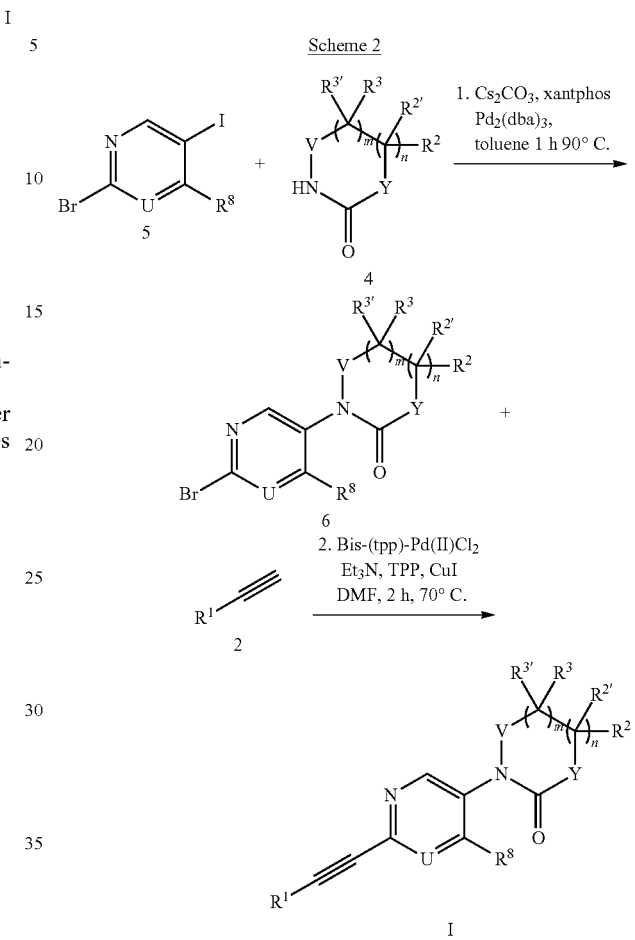

An ethynyl-pyridine or ethynyl-pyrimidine compound of formula I can be obtained for example by substitution of 2-bromo-5-iodo-pyridine or pyrimidine 5 with an appropriate lactam, cyclic carbamate, cyclic urea or pyrazolidin-3-one derivative 4 in presence of a base such as cesium carbonate and using xantphos and $Pd_2(dba)_3$ in a solvent like toluene yielding the desired 2-bromo-pyridine or pyrimidine derivatives 6. Sonogashira coupling of 6 with an appropriately substituted arylacetylene 2 yields ethynyl-pyridine or ethynyl-pyrimidine compound of formula I.

Biological Assay and Data

Intracellular $Ca^{2+}$ Mobilization Assay

A monoclonal HEK-293 cell line stably transfected with a cDNA encoding for the human mGlu5a receptor was generated; for the work with mGlu5 Positive Allosteric Modulators (PAMs), a cell line with low receptor expression levels and low constitutive receptor activity was selected to allow the differentiation of agonistic versus PAM activity. Cells were cultured according to standard protocols (Freshney, 2000) in Dulbecco's Modified Eagle Medium with high glucose supplemented with 1 mM glutamine, 10% (vol/vol) heat-inactivated bovine calf serum, Penicillin/Streptomycin, 50 μg/ml hygromycin and 15 μg/ml blasticidin (all cell culture reagents and antibiotics from Invitrogen, Basel, Switzerland).

About 24 hrs before an experiment, 5×10⁴ cells/well were seeded in poly-D-lysine coated, black/clear-bottomed 96-well plates. The cells were loaded with 2.5 µM Fluo-4AM in loading buffer (1×HBSS, 20 mM HEPES) for 1 hr at 37° C. and washed five times with loading buffer. The cells were transferred into a Functional Drug Screening System 7000 (Hamamatsu, Paris, France), and 11 half logarithmic serial dilutions of test compound at 37° C. were added and the cells were incubated for 10-30 min, with on-line recording of fluorescence. Following this pre-incubation step, the agonist L-glutamate was added to the cells at a concentration corresponding to $EC_{20}$ (typically around 80 µM) with on-line recording of fluorescence; in order to account for day-to-day variations in the responsiveness of cells, the $EC_{20}$ of glutamate was determined immediately ahead of each experiment by recording of a full dose-response curve of glutamate.

Responses were measured as peak increase in fluorescence minus basal (i.e. fluorescence without addition of L-glutamate), normalized to the maximal stimulatory effect obtained with saturating concentrations of L-glutamate. Graphs were plotted with the % maximal stimulatory using XLfit, a curve fitting program that iteratively plots the data using Levenburg Marquardt algorithm. The single site competition analysis equation used was $y = A + ((B-A)/(1+((x/C)^D)))$, where y is the % maximal stimulatory effect, A is the minimum y, B is the maximum y, C is the $EC_{50}$, x is the log 10 of the concentration of the competing compound and D is the slope of the curve (the Hill Coefficient). From these curves the $EC_{50}$ (concentration at which half maximal stimulation was achieved), the Hill coefficient as well as the maximal response in % of the maximal stimulatory effect obtained with saturating concentrations of L-glutamate were calculated.

Positive signals obtained during the pre-incubation with the PAM test compounds (i.e. before application of an $EC_{20}$ concentration of L-glutamate) were indicative of an agonistic activity, the absence of such signals were demonstrating the lack of agonistic activities. A depression of the signal observed after addition of the $EC_{20}$ concentration of L-glutamate was indicative of an inhibitory activity of the test compound.

In the list of examples are shown the corresponding results for compounds which all have $EC_{50}$<250 nM.

| Ex. | Structure | Name | $EC_{50}$ (nM) mGlu5PAM | Eff. (%) |
|---|---|---|---|---|
| 1 | 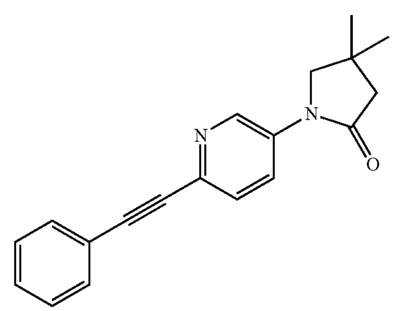 [SMILES: CC1(C)CC(=O)N(c2ccc(C#Cc3ccccc3)nc2)C1] | 4,4-Dimethyl-1-(6-phenylethynyl-pyridin-3-yl)-pyrrolidin-2-one | 49 | 75 |
| 2 | 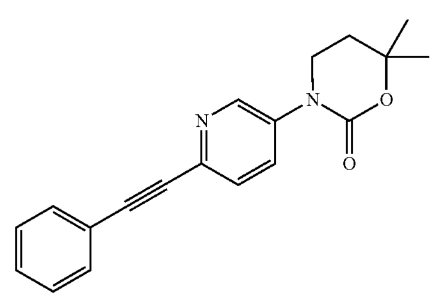 [SMILES: CC1(C)CCN(c2ccc(C#Cc3ccccc3)nc2)C(=O)O1] | 6,6-Dimethyl-3-(6-phenylethynyl-pyridin-3-yl)-[1,3]oxazinan-2-one | 96 | 85 |
| 3 | 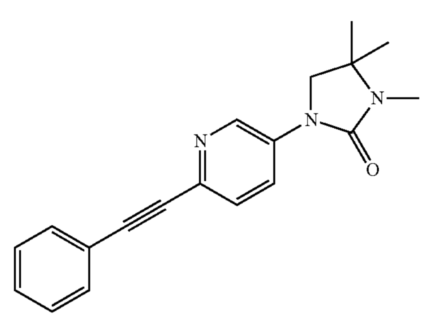 [SMILES: CN1C(=O)N(c2ccc(C#Cc3ccccc3)nc2)CC1(C)C] | 3,4,4-Trimethyl-1-(6-phenylethynyl-pyridin-3-yl)-imidazolidin-2-one | 15 | 45 |

-continued

| Ex. | Structure | Name | EC$_{50}$ (nM) mGlu5PAM | Eff. (%) |
|---|---|---|---|---|
| 4 | 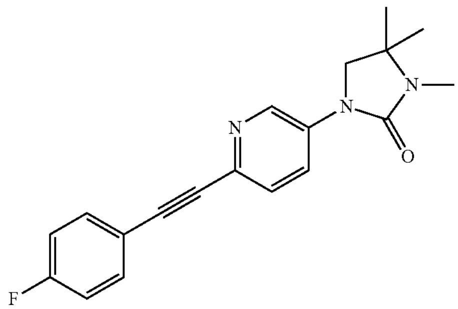 [SMILES: CN1C(=O)N(c2ccc(C#Cc3ccc(F)cc3)nc2)CC1(C)C] | 1-[6-(4-Fluoro-phenylethynyl)-pyridin-3-yl]-3,4,4-trimethyl-imidazolidin-2-one | 50 | 44 |
| 5 | 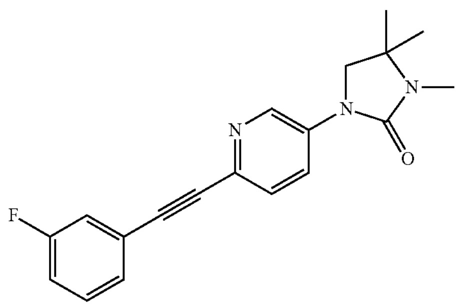 [SMILES: CN1C(=O)N(c2ccc(C#Cc3cccc(F)c3)nc2)CC1(C)C] | 1-[6-(3-Fluoro-phenylethynyl)-pyridin-3-yl]-3,4,4-trimethyl-imidazolidin-2-one | 19 | 42 |
| 6 | 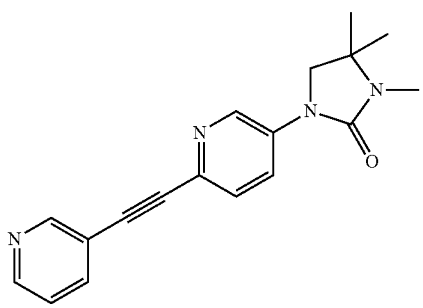 [SMILES: CN1C(=O)N(c2ccc(C#Cc3cccnc3)nc2)CC1(C)C] | 3,4,4-Trimethyl-1-(6-pyridin-3-ylethynyl-pyridin-3-yl)-imidazolidin-2-one | 241 | 36 |
| 7 | 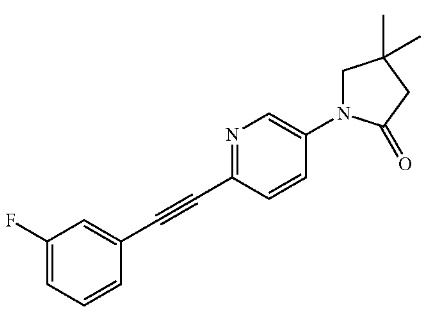 [SMILES: CC1(C)CC(=O)N(c2ccc(C#Cc3cccc(F)c3)nc2)C1] | 1-[6-(3-Fluoro-phenylethynyl)-pyridin-3-yl]-4,4-dimethyl-pyrrolidin-2-one | 39 | 62 |
| 8 | 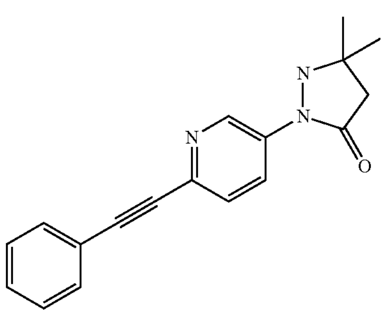 [SMILES: CC1(C)CC(=O)N(c2ccc(C#Cc3ccccc3)nc2)N1] | 5,5-Dimethyl-2-(6-phenylethynyl-pyridin-3-yl)-pyrazolidin-3-one | 62 | 56 |

-continued

| Ex. | Structure | Name | EC$_{50}$ (nM) mGlu5PAM | Eff. (%) |
|---|---|---|---|---|
| 9 | 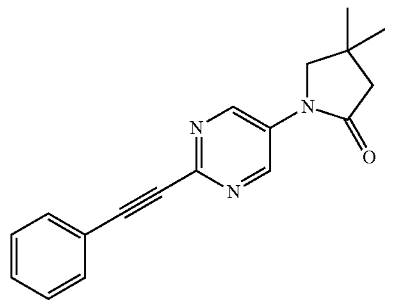 | 4,4-Dimethyl-1-(6-phenylethynyl-pyrimidin-3-yl)-pyrrolidin-2-one | 36 | 39 |
| 10 | 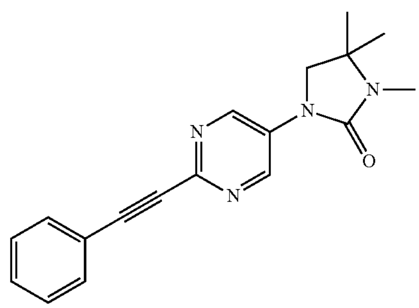 [SMILES: CN1C(=O)N(c2cnc(C#Cc3ccccc3)nc2)CC1(C)C] | 3,4,4-Trimethyl-1-(2-phenylethynyl-pyrimidin-5-yl)-imidazolidin-2-one | — | — |
| 11 | 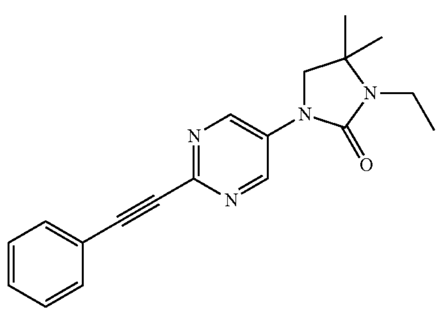 [SMILES: CCN1C(=O)N(c2cnc(C#Cc3ccccc3)nc2)CC1(C)C] | 3-Ethyl-4,4-dimethyl-1-(2-phenylethynyl-pyrimidin-5-yl)-imidazolidin-2-one | 79 | 52 |
| 12 | 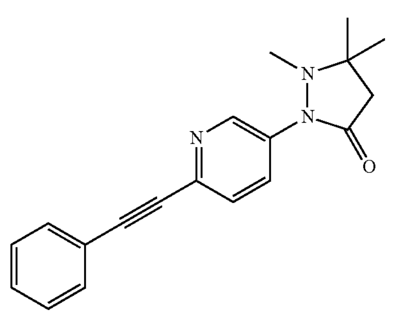 [SMILES: CN1N(c2ccc(C#Cc3ccccc3)nc2)C(=O)CC1(C)C] | 1,5,5-Trimethyl-2-(6-phenylethynyl-pyridin-3-yl)-pyrazolidin-3-one | 40 | 66 |
| 13 | 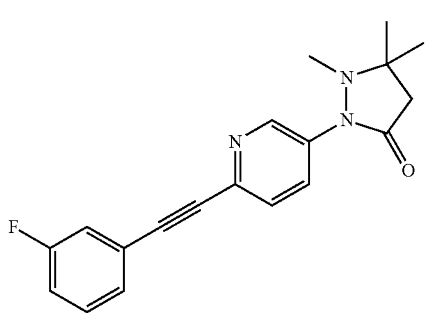 [SMILES: CN1N(c2ccc(C#Cc3cccc(F)c3)nc2)C(=O)CC1(C)C] | 2-[6-(3-Fluoro-phenylethynyl)-pyridin-3-yl]-1,5,5-trimethyl-pyrazolidin-3-one | 38 | 63 |

-continued

| Ex. | Structure | Name | EC$_{50}$ (nM) mGlu5PAM | Eff. (%) |
|---|---|---|---|---|
| 14 | 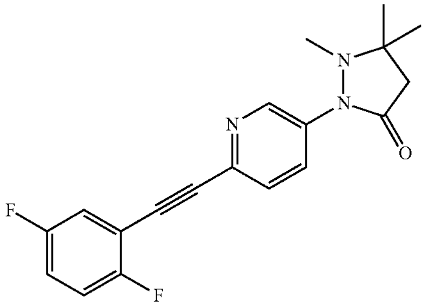 [SMILES: CN1N(c2ccc(C#Cc3cc(F)ccc3F)nc2)C(=O)CC1(C)C] | 2-[6-(2,5-Difluoro-phenylethynyl)-pyridin-3-yl]-1,5,5-trimethyl-pyrazolidin-3-one | 53 | 57 |
| 15 | 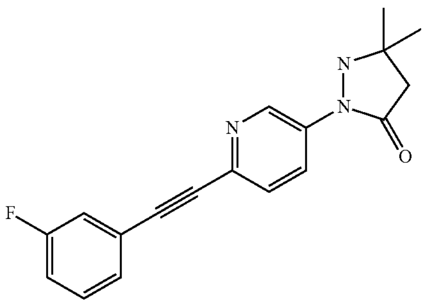 [SMILES: CC1(C)CC(=O)N(c2ccc(C#Cc3cccc(F)c3)nc2)N1] | 2-[6-(3-Fluoro-phenylethynyl)-pyridin-3-yl]-5,5-dimethyl-pyrazolidin-3-one | 68 | 38 |
| 16 | 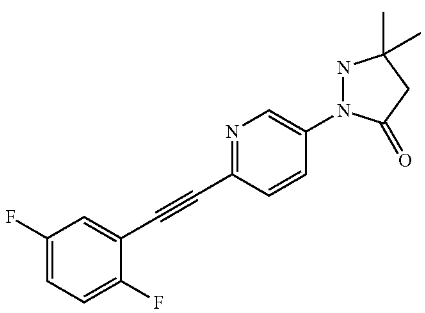 [SMILES: CC1(C)CC(=O)N(c2ccc(C#Cc3cc(F)ccc3F)nc2)N1] | 2-[6-(2,5-Difluoro-phenylethynyl)-pyridin-3-yl]-5,5-dimethyl-pyrazolidin-3-one | 40 | 41 |

EXPERIMENTAL SECTION

Example 1

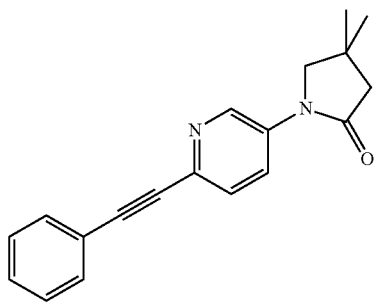

4,4-Dimethyl-1-(6-phenylethynyl-pyridin-3-yl)-pyrrolidin-2-one

Step 1: 5-Bromo-2-phenylethynyl-pyridine

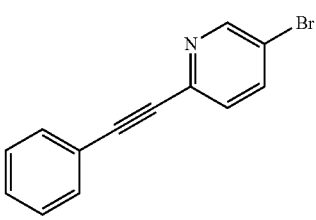 [SMILES: Brc1ccc(C#Cc2ccccc2)nc1]

Bis-(triphenylphosphine)-palladium(II)dichloride (62 mg, 0.088 mmol, 0.05 equiv.) was dissolved in 5 ml THF. (500 mg, 1.76 mmol) 5-Bromo-2-iodopyridine and phenylacetylene (216 mg, 2.11 mmol, 1.2 equiv.) were added at room temperature. Triethylamine (0.74 ml, 5.28 mmol, 3 equiv.) and copper(I)iodide (10 mg, 0.053 mmol, 0.03 equiv.) were added and the mixture was stirred for 16 hours at 60° C. The reaction mixture was evaporated to dryness and loaded directly to a silica gel column. The crude product was purified by flash chromatography on a silica gel column eluting with a heptane:ethyl acetate gradient 100:0 to 90:10. The desired 5-bromo-2-phenylethynyl-pyridine (354 mg, 78% yield) was obtained as a light yellow solid, MS: m/e=258.0/259.9 (M+H⁺).

Step 2: 4,4-Dimethyl-1-(6-phenylethynyl-pyridin-3-yl)-pyrrolidin-2-one

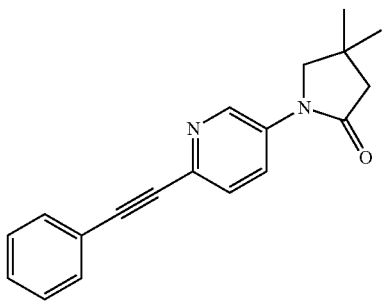

To a suspension of 5-bromo-2-phenylethynyl-pyridine (Example 1, step 1) (40 mg, 0.155 mmol), 4,4-dimethylpyrrolidine-2-one (21 mg, 0.186 mmol, 1.2 equiv.), potassium carbonate (64 mg, 0.465 mmol, 3 equiv.) and N,N'-dimethylethylenediamine (1.4 mg, 0.015 mmol, 0.1 equiv.) in 1 ml of dioxane was added under argon atmosphere copper(I)iodide (3 mg, 0.015 mmol, 0.1 equiv.). The mixture was stirred overnight at 100° C. The reaction mixture was cooled and extracted with saturated NaHCO₃ solution and two times with ethyl acetate. The organic layers were extracted with brine, combined, dried over sodium sulfate and evaporated to dryness. The crude product was purified by flash chromatography on a silica gel column eluting with a heptane:ethyl acetate gradient 100:0 to 30:70. The desired 4,4-dimethyl-1-(6-phenylethynyl-pyridin-3-yl)-pyrrolidin-2-one (30 mg, 67% yield) was obtained as a white solid, MS: m/e=291.1 (M+H³⁰).

Example 2

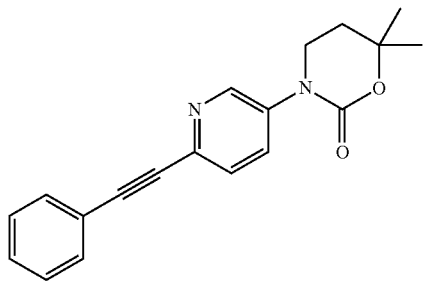

6,6-Dimethyl-3-(6-phenylethynyl-pyridin-3-yl)-[1,3]oxazinan-2-one

Step 1: (3-Hydroxy-3-methyl-butyl)-carbamic acid benzyl ester

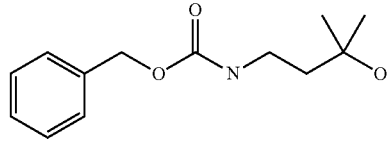 [SMILES: CC(C)(O)CCNC(=O)OCc1ccccc1]

(10 g, 42.1 mmol) Methyl 3-(benzyloxycarbonylamino) propanoate (CAS 54755-77-0) was dissolved in THF (150 ml) and cooled to 0-5° C. 3N Methylmagnesium bromide in THF (56.2 ml, 120 mmol, 4 equiv.) was added drop wise and the mixture stirred for 1 hour at 0-5° C. The reaction mixture was extracted with saturated NH₄Cl solution and two times with EtOAc. The organic layers were dried over Na₂SO₄ and evaporated to dryness. The desired (3-hydroxy-3-methyl-butyl)-carbamic acid benzyl ester (11.6 g, quant.) was obtained as a colorless oil, MS: m/e=238.1 (M+H⁺) and used in the next step without further purification.

Step 2: 6,6-dimethyl-[1,3]oxazinan-2-one

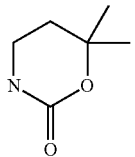

(11.6 g, 48.9 mmol) (3-Hydroxy-3-methyl-butyl)-carbamic acid benzyl ester (Example 72, step 1) was dissolved in THF (250 ml) and sodium hydride (60%, 5.2 g, 108 mmol, 2.2 equiv.) was added in portions. The mixture was stirred for 3 hours at room temperature. 5 ml saturated NaHCO₃ solution was added carefully and the mixture was evaporated with isolute to dryness. The crude product was purified by flash chromatography by directly loading the residue onto a silica gel column and eluting with an ethyl acetate:methanol gradient 100:0 to 90:10. The desired 6,6-dimethyl-[1,3]oxazinan-2-one (3.2 g, 51% yield) was obtained as a yellow solid, MS: m/e=130.1 (M+H⁺).

Step 3: 6,6-Dimethyl-3-(6-phenylethynyl-pyridin-3-yl)-[1,3]oxazinan-2-one

The title compound was obtained as a white solid, MS: m/e=307.2 (M+H⁺), using chemistry similar to that described in Example 1, step 2 from 5-bromo-2-phenylethynyl-pyridine (Example 1, step 1) and 6,6-dimethyl-[1,3]oxazinan-2-one (Example 2, step 2).

Example 3

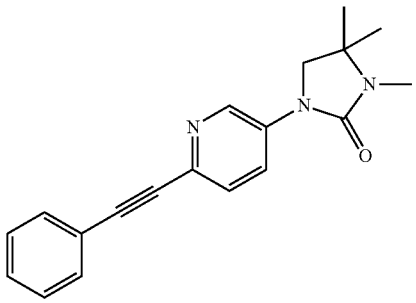

3,4,4-Trimethyl-1-(6-phenylethynyl-pyrimidin-3-yl)-imidazolidin-2-one

Step 1: 1-(6-Bromo-pyridin-3-yl)-4,4-dimethyl-imidazolidin-2-one

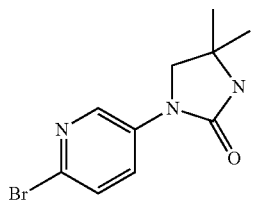

To a suspension of 2-bromo-5-iodopyridine (1.0 g, 3.52 mmol), 4,4-dimethyl-imidazolidin-2-one (CAS 24572-33-6) (400 mg, 3.52 mmol, 1.0 equiv.), cesium carbonate (1.72 g, 5.28 mmol, 1.5 equiv.), and 4,5-bis(diphenylphosphino)-9,9-dimethylxanthene (xantphos) (82 mg, 0.141 mmol, 0.04 equiv.) in 10 ml of toluene was added under argon atmosphere tris(dibenzylideneacetone)dipalladium(0) chloroform adduct ($Pd_2(dba)_3$*$CHCl_3$) (73 mg, 0.07 mmol, 0.02 equiv.). The mixture was stirred for 1 hour at 100° C. The mixture was directly loaded on a 50 g silicagel column and was eluted with an heptan:ethyl acetate gradient 100:0 to 0:100 and an ethyl acetate:methanol gradient 100:0 to 80:20. The desired 1-(6-bromo-pyridin-3-yl)-4,4-dimethyl-imidazolidin-2-one (810 mg, 85% yield) was obtained as a light yellow solid, MS: m/e=207.1/272.1 ($M+H^+$).

Step 2: 1-(6-Bromo-pyridin-3-yl)-3,4,4-trimethyl-imidazolidin-2-one

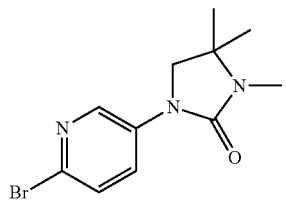 [SMILES: CN1C(=O)N(c2ccc(Br)nc2)CC1(C)C]

(810 mg, 3.0 mmol) 1-(6-Bromo-pyridin-3-yl)-4,4-dimethyl-imidazolidin-2-one (Example 3, step 1) was dissolved in DMF (8 ml) and cooled to 0-5° C. Iodomethane (640 mg, 280 μl, 4.5 mmol, 1.5 equiv.) and NaH (60%) (156 mg, 3.9 mmol, 1.3 equiv.) were added and the mixture was stirred for 2 hours at 0-5° C. The reaction mixture was treated with sat. $NaHCO_3$ solution and extracted two times with EtOAc. The organic layers were extracted with water and brine, dried over $Na_2SO_4$ and evaporated to dryness. The crude product was purified by flash chromatography on a silica gel column eluting with a heptane:ethyl acetate gradient 100:0 to 0:100. The desired 1-(6-bromo-pyridin-3-yl)-3,4,4-trimethyl-imidazolidin-2-one (800 mg, 94% yield) was obtained as a yellow solid, MS: m/e=284.1/286.0 ($M+M^+$).

Step 3: 3,4,4-Trimethyl-1-(6-phenylethynyl-pyridin-3-yl)-imidazolidin-2-one

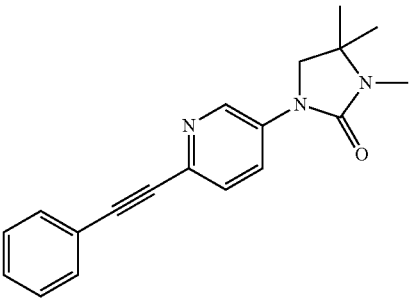

Bis-(triphenylphosphine)-palladium(II)dichloride (6 mg, 8.5 μmol, 0.03 equiv.) was dissolved in 1 ml DMF. (80 mg, 282 μmol) 1-(6-Bromo-pyridin-3-yl)-3,4,4-trimethyl-imidazolidin-2-one (Example 3, step 2) and phenylacetylene (58 mg, 563 μmol, 2 equiv.) were added at room temperature. Triethylamine (118 μl 0.845 mmol, 3 equiv.), triphenylphosphine (4.4 mg, 16.9 μmol, 0.06 equiv.) and copper(I)iodide (1.6 mg, 8.45 μmol, 0.03 equiv.) were added and the mixture was stirred for 4 hours at 90° C. The reaction mixture was evaporated to dryness with Isolute® and the crude product was purified by flash chromatography by directly loading the solid onto a silica gel column and eluting with an ethyl acetate: heptane gradient 0:100 to 100:0. The desired 3,4,4-trimethyl-1-(6-phenylethynyl-pyridin-3-yl)-imidazolidin-2-one (52 mg, 61% yield) was obtained as a yellow solid, MS: m/e=306.2 ($M+H^+$).

Example 4

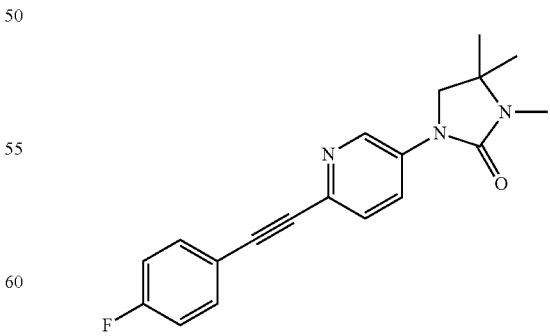

1-[6-(4-Fluoro-phenylethynyl)-pyridin-3-yl]-3,4,4-trimethyl-imidazolidin-2-one

The title compound was obtained as a yellow solid, MS: m/e=324.2 ($M+H^+$), using chemistry similar to that described in Example 3, step 3 from 1-(6-bromo-pyridin-3-yl)-3,4,4-trimethyl-imidazolidin-2-one (Example 3, step 2) and 4-fluorophenylacetylene.

Example 5

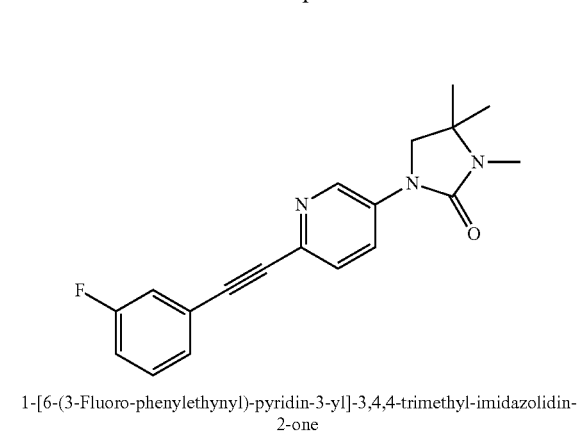

1-[6-(3-Fluoro-phenylethynyl)-pyridin-3-yl]-3,4,4-trimethyl-imidazolidin-2-one

The title compound was obtained as a yellow solid, MS: m/e=324.2 (M+H$^+$), using chemistry similar to that described in Example 3, step 3 from 1-(6-bromo-pyridin-3-yl)-3,4,4-trimethyl-imidazolidin-2-one (Example 3, step 2) and 3-fluorophenylacetylene.

Example 6

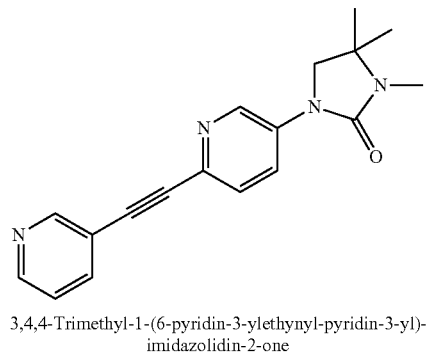 [SMILES: CN1C(=O)N(c2ccc(C#Cc3cccnc3)nc2)CC1(C)C]

3,4,4-Trimethyl-1-(6-pyridin-3-ylethynyl-pyridin-3-yl)-imidazolidin-2-one

Step 1: 5-Bromo-2-pyridin-3-ylethynyl-pyridine

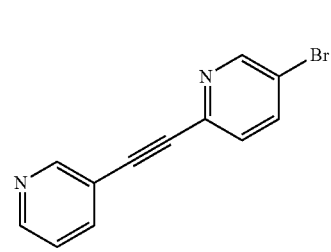 [SMILES: Brc1ccc(C#Cc2cccnc2)nc1]

The title compound was obtained as a yellow solid, MS: m/e=259.0/260.9 (M+H$^+$), using chemistry similar to that described in Example 1, step 1 from 5-bromo-2-iodopyridine and 3-ethynylpyridine.

Step 2: 4,4-Dimethyl-1-(6-pyridin-3-ylethynyl-pyridin-3-yl)-imidazolidin-2-one

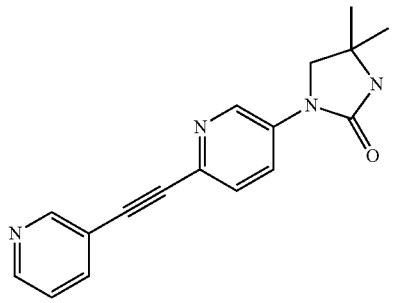 [SMILES: CC1(C)CN(c2ccc(C#Cc3cccnc3)nc2)C(=O)N1]

The title compound was obtained as a white solid, MS: m/e=293.1 (M+H$^+$), using chemistry similar to that described in Example 1, step 2 from 5-bromo-2-pyridin-3-ylethynyl-pyridine (Example 6, step 1) and 4,4-dimethyl-imidazolidin-2-one (CAS 24572-33-6).

Step 3: 3,4,4-Trimethyl-1-(6-pyridin-3-ylethynyl-pyridin-3-yl)-imidazolidin-2-one The title compound was obtained as a white solid, MS: m/e=307.2 (M+H$^+$), using chemistry similar to that described in Example 3, step 2 from 4,4-Dimethyl-1-(6-pyridin-3-ylethynyl-pyridin-3-yl)-imidazolidin-2-one (Example 6, step 2) and iodomethane.

Example 7

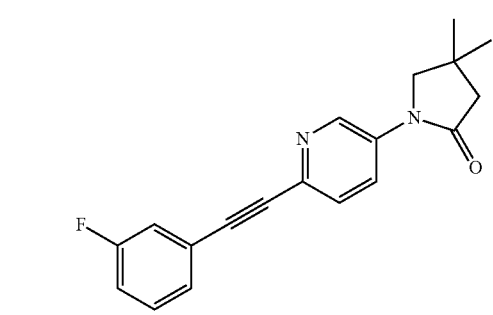

1-[6-(3-Fluoro-phenylethynyl)-pyridin-3-yl]-4,4-dimethyl-pyrrolidin-2-one

The title compound was obtained as a white solid, MS: m/e=309.1 (M+H$^+$), using chemistry similar to that described in Example 1, step 1 and step 2 from 5-bromo-2-iodopyridine, 3-fluorophenylacetylene and 4,4-dimethylpyrrolidine-2-one.

Example 8

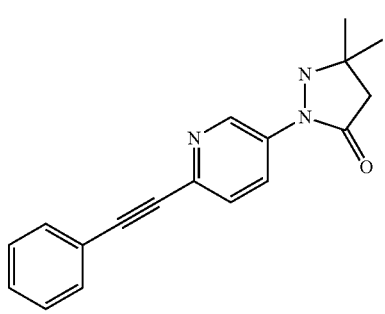

5,5-Dimethyl-2-(6-phenylethynyl-pyridin-3-yl)-pyrazolidin-3-one

The title compound was obtained as a white solid, MS: m/e=292.1 (M+H⁺), using chemistry similar to that described in Example 1, step 2 from 5-bromo-2-phenylethynyl-pyridine (Example 1, step 1) and 5,5-dimethyl-pyrazolidin-3-one (CAS 42953-82-2).

Example 9

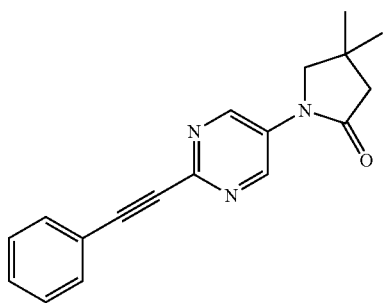

4,4-Dimethyl-1-(6-phenylethynyl-pyrimidin-3-yl)-pyrrolidin-2-one

Step 1: 1-(2-Bromo-pyrimidin-5-yl)-4,4-dimethyl-pyrrolidin-2-one

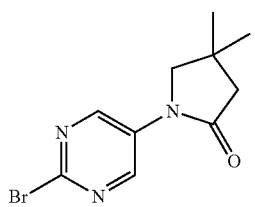

The title compound was obtained as a light yellow solid, MS: m/e=270.1/272.1 (M+H⁺), using chemistry similar to that described in Example 3, step 1 from 2-bromo-5-iodopyrimidine and 4,4-dimethylpyrrolidine-2-one.

Step 2: 4,4-Dimethyl-1-(6-phenylethynyl-pyrimidin-3-yl)-pyrrolidin-2-one

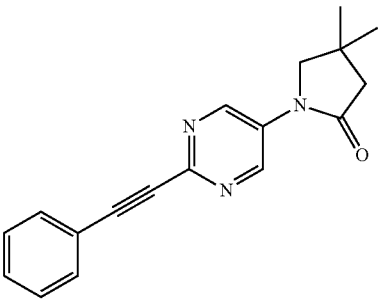 [SMILES: CC1(C)CC(=O)N(c2cnc(C#Cc3ccccc3)nc2)C1]

The title compound was obtained as a light brown solid, MS: m/e=292.3 (M+H⁺), using chemistry similar to that described in Example 1, step 3 from 1-(2-bromo-pyrimidin-5-yl)-4,4-dimethyl-pyrrolidin-2-one (Example 9, step 1) and phenylacetylene.

Example 10

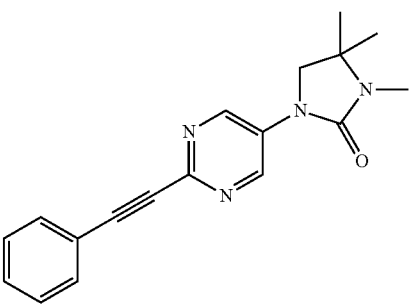

3,4,4-Trimethyl-1-(2-phenylethynyl-pyrimidin-5-yl)-imidazolidin-2-one

Step 1: 1-(2-Bromo-pyrimidin-5-yl)-4,4-dimethyl-imidazolidin-2-one

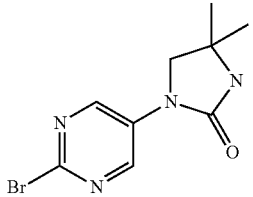

The title compound was obtained as a white solid, MS: m/e=271.2/273.1 (M+H⁺), using chemistry similar to that described in Example 3, step 1 from 2-bromo-5-iodopyrimidine and 4,4-dimethyl-imidazolidin-2-one (CAS 24572-33-6).

Step 2: 4,4-Dimethyl-1-(2-phenylethynyl-pyrimidin-5-yl-imidazolidin-2-one

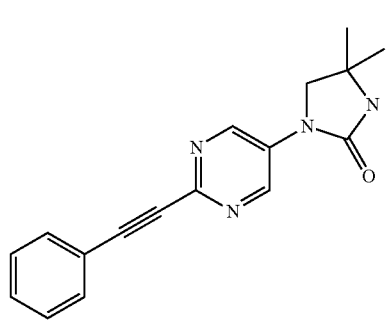 [SMILES: CC1(C)CN(c2cnc(C#Cc3ccccc3)nc2)C(=O)N1]

The title compound was obtained as a white solid, MS: m/e 293.0 (M+H⁺), using chemistry similar to that described in Example 3, step 3 from 1-(2-bromo-pyrimidin-5-yl)-4,4-dimethyl-imidazolidin-2-one (Example 10, step 1) and phenylacetylene.

Step 2: 3,4,4-Trimethyl-1-(2-phenylethynyl-pyrimidin-5-yl)-imidazolidin-2-one

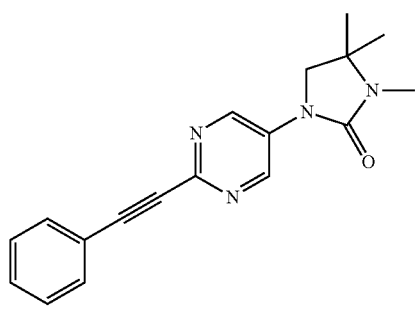 [SMILES: CN1C(=O)N(c2cnc(C#Cc3ccccc3)nc2)CC1(C)C]

The title compound was obtained as a white solid, MS: m/e=307.2 (M+H⁺), using chemistry similar to that described in Example 3, step 2 from 4,4-dimethyl-1-(2-phenylethynyl-pyrimidin-5-yl)-imidazolidin-2-one (Example 10, step 2) and iodomethane.

Example 11

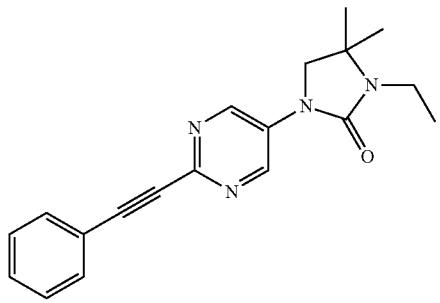

3-Ethyl-4,4-dimethyl-1-(2-phenylethynyl-pyrimidin-5-yl)-imidazolidin-2-one

The title compound was obtained as a light yellow solid, MS: m/e=321.4 (M+H⁺), using chemistry similar to that described in Example 3, step 2 from 4,4-dimethyl-1-(2-phenylethynyl-pyrimidin-5-yl)-imidazolidin-2-one (Example 10, step 2) and iodoethane.

Example 12

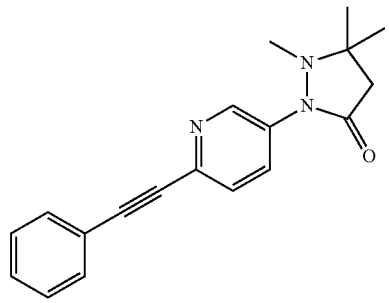

1,5,5-Trimethyl-2-(6-phenylethynyl-pyridin-3-yl)-pyrazolidin-3-one

Step 1: 2-(6-Bromo-pyridin-3-yl)-5,5-dimethyl-pyrazolidin-3-one

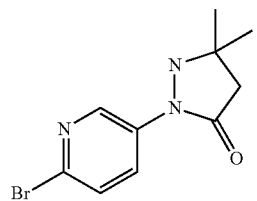

The title compound was obtained as a yellow oil, MS: m/e=270.3/272.3 (M+H⁺), using chemistry similar to that described in Example 3, step 1 from 2-bromo-5-iodopyridine and 5,5-dimethyl-pyrazolidin-3-one (CAS 42953-82-2) by using dioxane instead of toluene as solvent.

Step 2: 2-(6-Bromo-pyridin-3-yl)-1,5,5-trimethyl-pyrazolidin-3-one

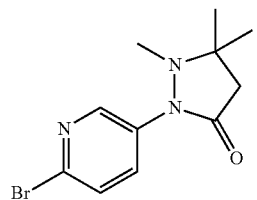 [SMILES: CN1N(c2ccc(Br)nc2)C(=O)CC1(C)C]

A suspension of 2-(6-bromo-pyridin-3-yl)-5,5-dimethyl-pyrazolidin-3-one (Example 12, step 1) (800 mg, 2.96 mmol) and formic acid (0.57 ml, 14.8 mmol, 5 equiv.) in water (8 ml) was heated to 100° C. At this temperature formaldehyde (36% in water) (1.13 ml, 14.8 mmol, 5 equiv.) was added drop wise. The mixture was stirred overnight at 100° C. The reaction mixture was cooled and basified carefully with 2N NaOH and extracted two times with a small amount of dichloromethane. The organic layers were loaded directly on a silica gel column and the crude product was purified by flash chromatography eluting with a heptane:ethyl acetate gradient 100:0 to 0:100. The desired 2-(6-bromo-pyridin-3-yl)-1,5,5-trimethyl-pyrazolidin-3-one (380 mg, 45% yield) was obtained as a colorless oil, MS: m/e=284.3/286.3 (M+H⁺).

Step 3: 1,5,5-Trimethyl-2-(6-phenylethynyl-pyridin-3-yl)-pyrazolidin-3-one

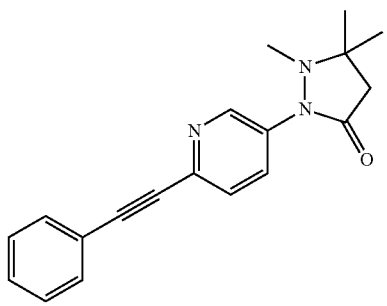 [SMILES: CN1N(c2ccc(C#Cc3ccccc3)nc2)C(=O)CC1(C)C]

The title compound was obtained as a yellow oil, MS: m/e=306.5 (M+H⁺), using chemistry similar to that described in Example 3, step 3 from 2-(6-bromo-pyridin-3-yl)-1,5,5-trimethyl-pyrazolidin-3-one (Example 12, step 2) and phenylacetylene.

Example 13

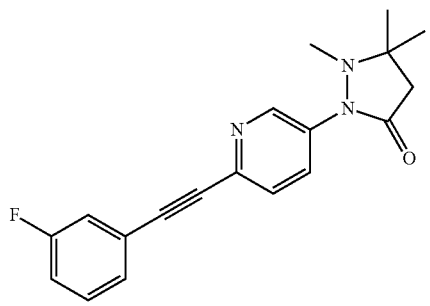

2-[6-(3-Fluoro-phenylethynyl)-pyridin-3-yl]-1,5,5-trimethyl-pyrazolidin-3-one

The title compound was obtained as a yellow oil, MS: m/e=324.4 (M+H⁺), using chemistry similar to that described in Example 3, step 3 from 2-(6-bromo-pyridin-3-yl)-1,5,5-trimethyl-pyrazolidin-3-one (Example 12, step 2) and 3-fluorophenylacetylene.

Example 14

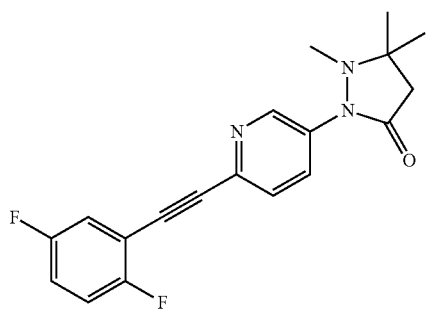

2-[6-(2,5-Difluoro-phenylethynyl)-pyridin-3-yl]-1,5,5-trimethyl-pyrazolidin-3-one The title compound was obtained as a yellow solid, MS: m/e=342.4 (M+H⁺), using chemistry similar to that described in Example 3, step 3 from 2-(6-bromo-pyridin-3-yl)-1,5,5-trimethyl-pyrazolidin-3-one (Example 12, step 2) and 2,5-difluorophenylacetylene.

Example 15

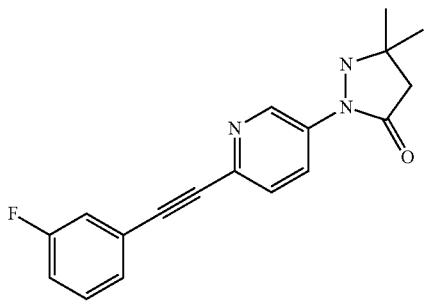

2-[6-(3-Fluoro-phenylethynyl)-pyridin-3-yl]-5,5-dimethyl-pyrazolidin-3-one

The title compound was obtained as a brown oil, MS: m/e=310.4 (M+H⁺), using chemistry similar to that described in Example 3, step 3 from 2-(6-bromo-pyridin-3-yl)-5,5-dimethyl-pyrazolidin-3-one (Example 12, step 1) and 3-fluorophenylacetylene.

Example 16

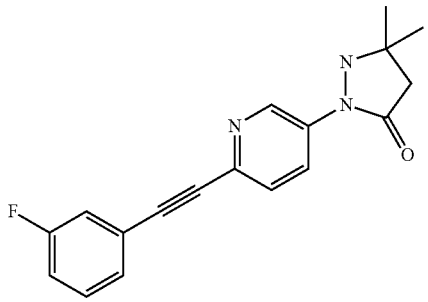

2-[6-(2,5-Difluoro-phenylethynyl)-pyridin-3-yl]-5,5-dimethyl-pyrazolidin-3-one

The title compound was obtained as a light yellow solid, MS: m/e=328.4 (M+H⁺), using chemistry similar to that described in Example 3, step 3 from 2-(6-bromo-pyridin-3-yl)-5,5-dimethyl-pyrazolidin-3-one (Example 12, step 1) and 2,5-difluorophenylacetylene.

The compounds of formula (I) and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

As further mentioned earlier, the use of the compounds of formula (I) for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Pharmaceutical Compositions Comprising Compounds of the Invention:

Tablets of the following composition are produced in a conventional manner:

|  | mg/Tablet |
|---|---|
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

What is claimed:
1. A compound of formula

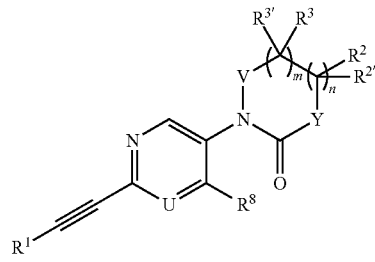

I wherein
U is N or CH,
$R^8$ is hydrogen, halogen, lower alkyl or lower alkoxy;
Y is —N($R^4$)— or —C($R^5R^{5'}$)—;
wherein $R^4$ is hydrogen or lower alkyl and $R^5/R^{5'}$ are independently hydrogen, hydroxy, lower alkyl or lower alkoxy;
V is —N($R^6$)— or —C($R^7R^{7'}$),
wherein $R^6$ is hydrogen or lower alkyl and $R^7/R^{7'}$ are independently from each other hydrogen, lower alkyl, $CH_2$-lower alkoxy or may form together with the carbon atom to which they are attached a $C_3$-$C_6$-cycloalkyl;
$R^1$ is phenyl or heteroaryl, which are optionally substituted by halogen, lower alkyl or lower alkoxy;
m is 0 or 1 and in case m is 1,
$R^3/R^{3'}$ are independently from each other hydrogen, lower alkyl, $CH_2$-lower alkoxy or may form together with the carbon atom to which they are attached a $C_3$-$C_6$-cycloalkyl;
n is 0 or 1 and in case n is 1,
$R^2/R^{2'}$ are independently hydrogen, lower alkyl or $CH_2$-lower alkoxy or may form together with the carbon atom to which they are attached a $C_3$-$C_6$-cycloalkyl;
or if m is 1 and n is 0, $R^3$ and $R^7$ may form together with the carbon atoms to which they are attached a $C_{4-6}$-cycloalkyl;
or if m is 1 and n is 1, $R^2$ and $R^3$ or $R^3$ and $R^7$ may form together with the carbon atoms to which they are attached a $C_{4-6}$-cycloalkyl;
or a pharmaceutically acceptable acid addition salt, a racemic mixture, or its corresponding enantiomer and/or optical isomer and/or stereoisomer thereof.

2. The compound of claim 1 having the formula

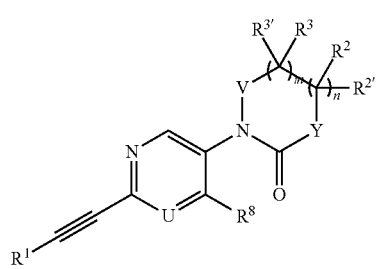

I-1 wherein
U is N or CH;
$R^8$ is hydrogen;
Y is $CH_2$, —N($CH_3$)— or —N($CH_2CH_3$)—;

V is CH₂, —NH— or —N(CH₃)—;
R¹ is phenyl or pyridinyl, which are optionally substituted by halogen;
m is 0 or 1 and in case m is 1,
R³/R³' are independently from each other hydrogen or lower alkyl,
n is 1;
R²/R²' are independently from each other hydrogen or lower alkyl;
or a pharmaceutically acceptable acid addition salt, a racemic mixture, or its corresponding enantiomer and/or optical isomer and/or stereoisomer thereof.

3. A compound of claim 2, selected from the group consisting of
4,4-Dimethyl-1-(6-phenylethynyl-pyridin-3-yl)-pyrrolidin-2-one,
3,4,4-Trimethyl-1-(6-phenylethynyl-pyridin-3-yl)-imidazolidin-2-one,
1-[6-(4-Fluoro-phenylethynyl)-pyridin-3-yl]-3,4,4-trimethyl-imidazolidin-2-one,
1-[6-(3-Fluoro-phenylethynyl)-pyridin-3-yl]-3,4,4-trimethyl-imidazolidin-2-one,
3,4,4-Trimethyl-1-(6-pyridin-3-ylethynyl-pyridin-3-yl)-imidazolidin-2-one,
1-[6-(3-Fluoro-phenylethynyl)-pyridin-3-yl]-4,4-dimethyl-pyrrolidin-2-one,
5,5-Dimethyl-2-(6-phenylethynyl-pyridin-3-yl)-pyrazolidin-3-one,
4,4-Dimethyl-1-(6-phenylethynyl-pyrimidin-3-yl)-pyrrolidin-2-one,
3,4,4-Trimethyl-1-(2-phenylethynyl-pyrimidin-5-yl)-imidazolidin-2-one,
3-Ethyl-4,4-dimethyl-1-(2-phenylethynyl-pyrimidin-5-yl)-imidazolidin-2-one,
1,5,5-Trimethyl-2-(6-phenylethynyl-pyridin-3-yl)-pyrazolidin-3-one,
2-[6-(3-Fluoro-phenylethynyl)-pyridin-3-yl]-1,5,5-trimethyl-pyrazolidin-3-one,
2-[6-(2,5-Difluoro-phenylethynyl)-pyridin-3-yl]-1,5,5-trimethyl-pyrazolidin-3-one,
2-[6-(3-Fluoro-phenylethynyl)-pyridin-3-yl]-5,5-dimethyl-pyrazolidin-3-one and
2-[6-(2,5-Difluoro-phenylethynyl)-pyridin-3-yl]-5,5-dimethyl-pyrazolidin-3-one.

4. The compound of claim 1 having the formula,

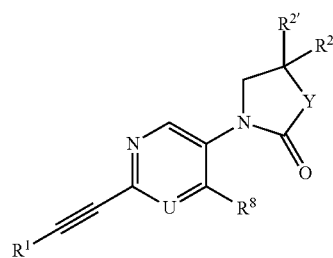

IA wherein
U is N or CH,
R⁸ is hydrogen, halogen, lower alkyl or lower alkoxy;
Y is —N(R⁴)— or —C(R⁵R⁵')—;
wherein R⁴ is hydrogen or lower alkyl and R⁵/R⁵' are independently hydrogen, hydroxy, lower alkyl or lower alkoxy;

R¹ is phenyl or heteroaryl, which are optionally substituted by halogen, lower alkyl or lower alkoxy;
R²/R²' are independently from each other hydrogen, lower alkyl or CH₂-lower alkoxy or may form together with the carbon atom to which they are attached a C₃-C₆-cycloalkyl;
or a pharmaceutically acceptable acid addition salt, a racemic mixture, or its corresponding enantiomer and/or optical isomer and/or stereoisomer thereof.

5. A compound of claim 4 of formula IA selected from the group consisting of
4,4-dimethyl-1-(6-phenylethynyl-pyridin-3-yl)-pyrrolidin-2-one,
3,4,4-trimethyl-1-(6-phenylethynyl-pyridin-3-yl)-imidazolidin-2-one,
1-[6-(4-fluoro-phenylethynyl)-pyridin-3-yl]-3,4,4-trimethyl-imidazolidin-2-one,
1-[6-(3-fluoro-phenylethynyl)-pyridin-3-yl]-3,4,4-trimethyl-imidazolidin-2-one,
3,4,4-trimethyl-1-(6-pyridin-3-ylethynyl-pyridin-3-yl)-imidazolidin-2-one,
1-[6-(3-fluoro-phenylethynyl)-pyridin-3-yl]-4,4-dimethyl-pyrrolidin-2-one,
4,4-dimethyl-1-(6-phenylethynyl-pyrimidin-3-yl)-pyrrolidin-2-one,
3,4,4-Trimethyl-1-(2-phenylethynyl-pyrimidin-5-yl)-imidazolidin-2-one and
3-Ethyl-4,4-dimethyl-1-(2-phenylethynyl-pyrimidin-5-yl)-imidazolidin-2-one.

6. The compound of claim 1 having the formula,

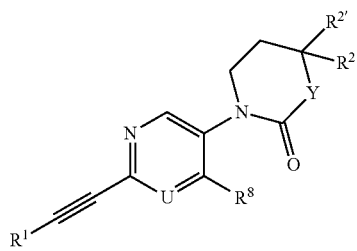

IB wherein
U is N or CH,
R⁸ is hydrogen, halogen, lower alkyl or lower alkoxy;
Y is —N(R⁴)— or —C(R⁵R⁵')—;
wherein R⁴ is hydrogen or lower alkyl and R⁵/R⁵' are independently hydrogen, hydroxy, lower alkyl or lower alkoxy;
R¹ is phenyl or heteroaryl, which are optionally substituted by halogen, lower alkyl or lower alkoxy;
R²/R²' are independently from each other hydrogen, lower alkyl or CH₂-lower alkoxy or may form together with the carbon atom to which they are attached a C₃-C₆-cycloalkyl;
or a pharmaceutically acceptable acid addition salt, a racemic mixture, or its corresponding enantiomer and/or optical isomer and/or stereoisomer thereof.

7. The compound of claim 1 having the formula,

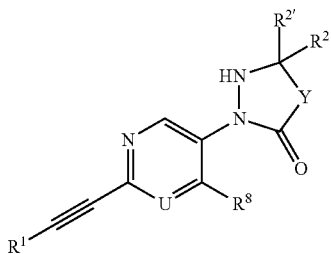

wherein
U is N or CH,
R⁸ is hydrogen, halogen, lower alkyl or lower alkoxy;
Y is —N(R⁴)— or —C(R⁵R⁵')—;
wherein R⁴ is hydrogen or lower alkyl and R⁵/R⁵' are independently hydrogen, hydroxy, lower alkyl or lower alkoxy;
R¹ is phenyl or heteroaryl, which are optionally substituted by halogen, lower alkyl or lower alkoxy;
R²/R²' are independently from each other hydrogen, lower alkyl or CH₂-lower alkoxy or may form together with the carbon atom to which they are attached a C₃-C₆-cycloalkyl;
or a pharmaceutically acceptable acid addition salt, a racemic mixture, or its corresponding enantiomer and/or optical isomer and/or stereoisomer thereof.

8. A compound of claim 7 of formula IC having the formula:
5,5-dimethyl-2-(6-phenylethynyl-pyridin-3-yl)-pyrazolidin-3-one.

9. The compound of claim 1 having the formula,

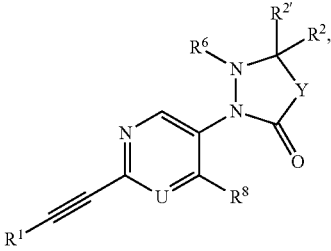

wherein
U is N or CH,
R⁸ is hydrogen, halogen, lower alkyl or lower alkoxy;
Y is —N(R⁴)— or —C(R⁵R⁵')—;
wherein R⁴ is hydrogen or lower alkyl and R⁵/R⁵' are independently hydrogen, hydroxy, lower alkyl or lower alkoxy;
R⁶ is hydrogen or lower alkyl
R¹ is phenyl or heteroaryl, which are optionally substituted by halogen, lower alkyl or lower alkoxy;
R²/R²' are independently from each other hydrogen, lower alkyl or CH₂-lower alkoxy or may form together with the carbon atom to which they are attached a C₃-C₆-cycloalkyl;
or a pharmaceutically acceptable acid addition salt, a racemic mixture, or its corresponding enantiomer and/or optical isomer and/or stereoisomer thereof.

10. A compound of claim 9 of formula ID selected from the group consisting of
1,5,5-Trimethyl-2-(6-phenylethynyl-pyridin-3-yl)-pyrazolidin-3-one,
2-[6-(3-Fluoro-phenylethynyl)-pyridin-3-yl]-1,5,5-trimethyl-pyrazolidin-3-one,
2-[6-(2,5-Difluoro-phenylethynyl)-pyridin-3-yl]-1,5,5-trimethyl-pyrazolidin-3-one,
2-[6-(3-Fluoro-phenylethynyl)-pyridin-3-yl]-5,5-dimethyl-pyrazolidin-3-one and
2-[6-(2,5-Difluoro-phenylethynyl)-pyridin-3-yl]-5,5-dimethyl-pyrazolidin-3-one.

11. A process for preparation of a compound of formula I as described in claim 1, comprising the variants
a) reacting a compound of formula

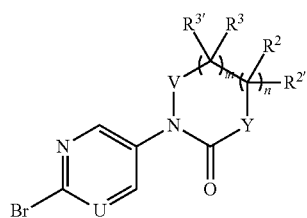

with a suitable aryl-acetylene of formula

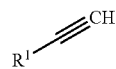

to a compound of formula

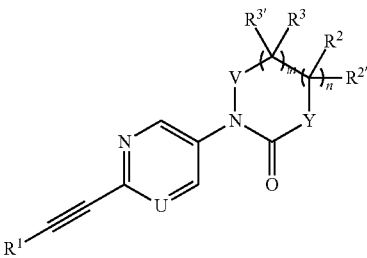

wherein the substituents are described in claim 1, or
b) reacting a compound of formula

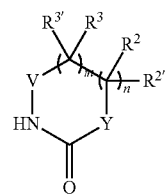

with a suitable compound of formula

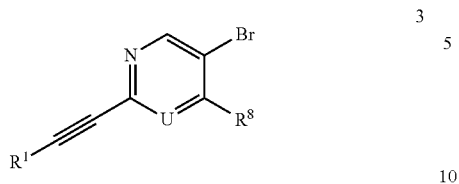

to a compound of formula

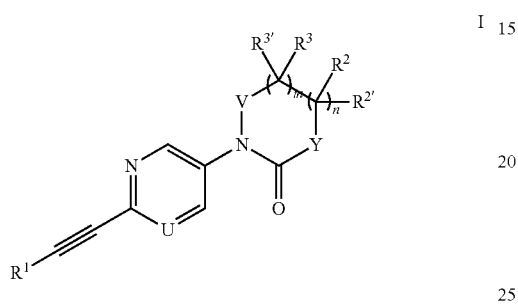

wherein the substituents are described in claim 1, and, if desired, converting the compounds obtained into pharmaceutically acceptable acid addition salts.

12. A pharmaceutical formulation comprising a compound of formula I together with a pharmaceutically acceptable excipient and/or carrier.

\* \* \* \* \*